United States Patent [19]
Wyssmann

[11] Patent Number: 5,741,275
[45] Date of Patent: Apr. 21, 1998

[54] DEVICE FOR THE INTENTIONAL AND CONTROLLABLE DISTRIBUTION OF A LIQUID OR VISCOUS MATERIAL

[76] Inventor: Max Wyssmann, Hochstrasse 7, Herzogenbuchsee, CH-3360, Switzerland

[21] Appl. No.: 196,074
[22] PCT Filed: Jun. 10, 1993
[86] PCT No.: PCT/CH93/00151
  § 371 Date: Feb. 14, 1994
  § 102(e) Date: Feb. 14, 1994
[87] PCT Pub. No.: WO93/25841
  PCT Pub. Date: Dec. 23, 1993

[30] Foreign Application Priority Data

Jun. 15, 1992 [CH] Switzerland .................. 1870/92

[51] Int. Cl.⁶ ............................................. A61M 37/00
[52] U.S. Cl. ..................................... 604/143; 604/145
[58] Field of Search ................................. 604/131, 132, 604/140, 141, 143, 145; 222/389, 386.5

[56] References Cited

U.S. PATENT DOCUMENTS

| | | |
|---|---|---|
| 4,414,298 | 11/1983 | Krenz . |
| 4,640,445 | 2/1987 | Yamada .................. 604/145 |
| 5,062,834 | 11/1991 | Gross et al. ............. 604/145 |
| 5,135,499 | 8/1992 | Tafani et al. ............ 604/140 |
| 5,304,128 | 4/1994 | Haber et al. ............ 604/143 |

FOREIGN PATENT DOCUMENTS

| | | |
|---|---|---|
| 0278954 | 1/1988 | European Pat. Off. . |
| 0278138 | 8/1988 | European Pat. Off. . |
| 0385916 | 9/1990 | European Pat. Off. . |
| 3532335 | 3/1987 | Germany . |
| 3718341 | 12/1988 | Germany . |
| 8804751 | 6/1988 | WIPO . |
| 8809187 | 12/1988 | WIPO . |
| 8809901 | 12/1988 | WIPO . |
| 8900044 | 3/1989 | WIPO . |
| 8908800 | 9/1989 | WIPO . |

OTHER PUBLICATIONS

Patent Abstracts of Japan, vol. 13, No. 295 (E-783), Jul. 7, 1989 and JP-A 10 76 665 (Shimada Kenji) Mar. 22, 1989.

*Primary Examiner*—Todd E. Manahan
*Attorney, Agent, or Firm*—Weiser & Associates P.C.

[57] ABSTRACT

A device for controllably dispensing a liquid or viscous material comprises a chamber which is subdivided by a piston into a pressurized gas chamber and a mass chamber. The container includes electrochemical, tablet-shaped, completely enclosed diffusion electrodes, aqueous electrolytes, a gas development cell containing a counter-electrode, an adjusting rheostat and contacts held by a clamping device in the bottom of the container. A vibration-dampening funnel-shaped container cap encloses the top end of the container and is totally compliant and shock-proof. The piston includes a piston seal which has a sealing lip monolithically connected to the piston with a space for a film of grease. An alternative embodiment has exchangeable electric elements and a refilling device. Other alternative embodiments have a simplified compact design for small sizes or for infusion devices or are associated with piston sensors.

37 Claims, 10 Drawing Sheets

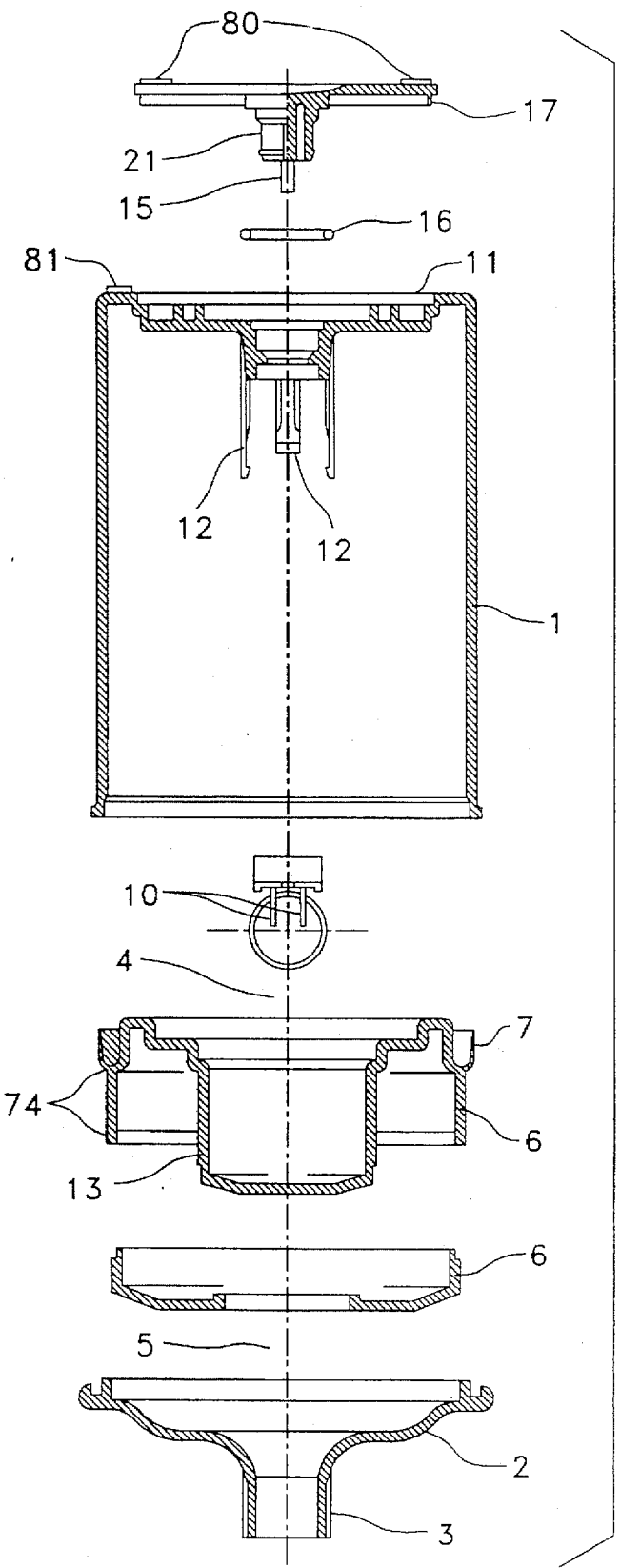
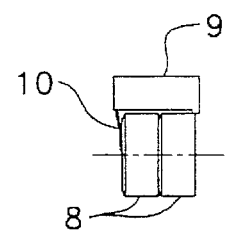
FIG. 1a
FIG. 1

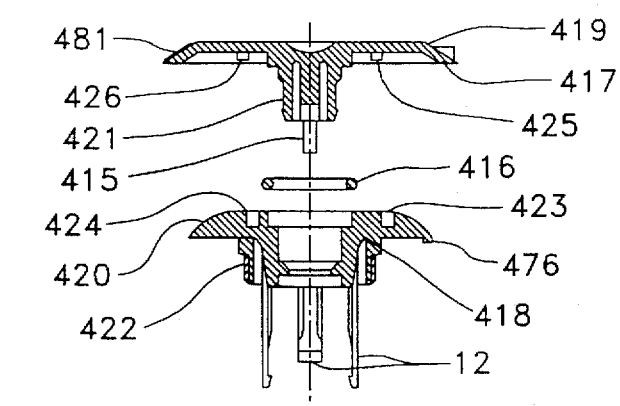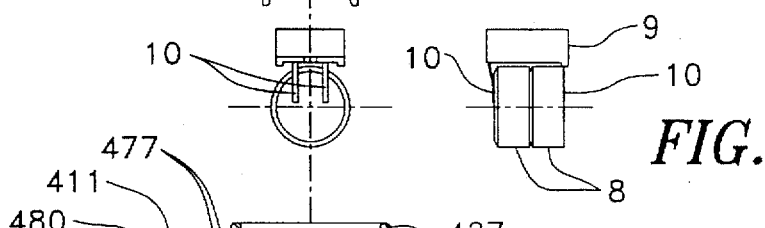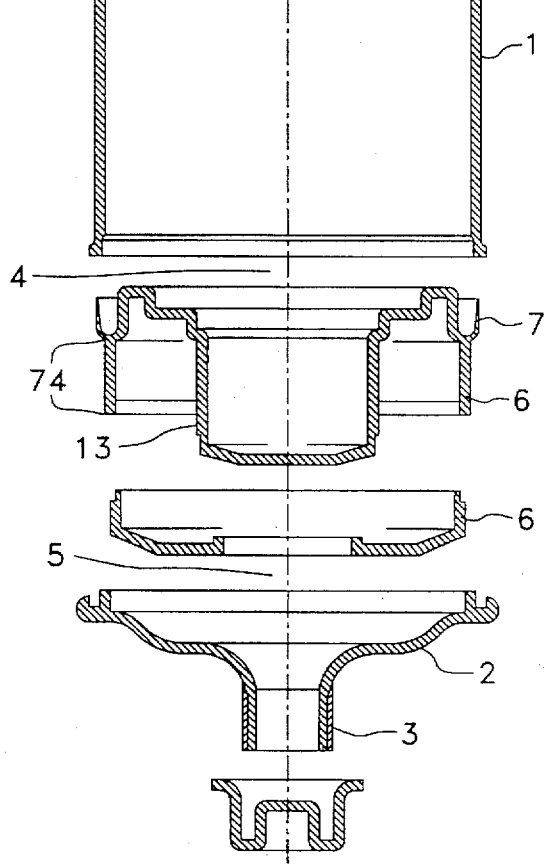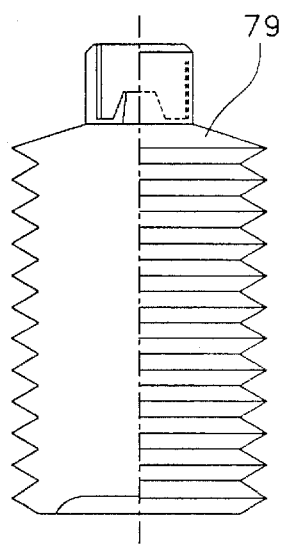
FIG. 4
FIG. 4a
FIG. 4b

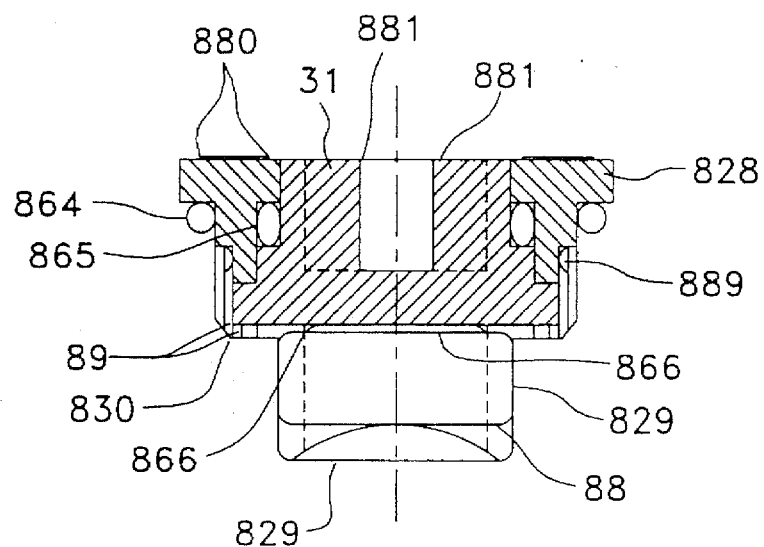
FIG. 8
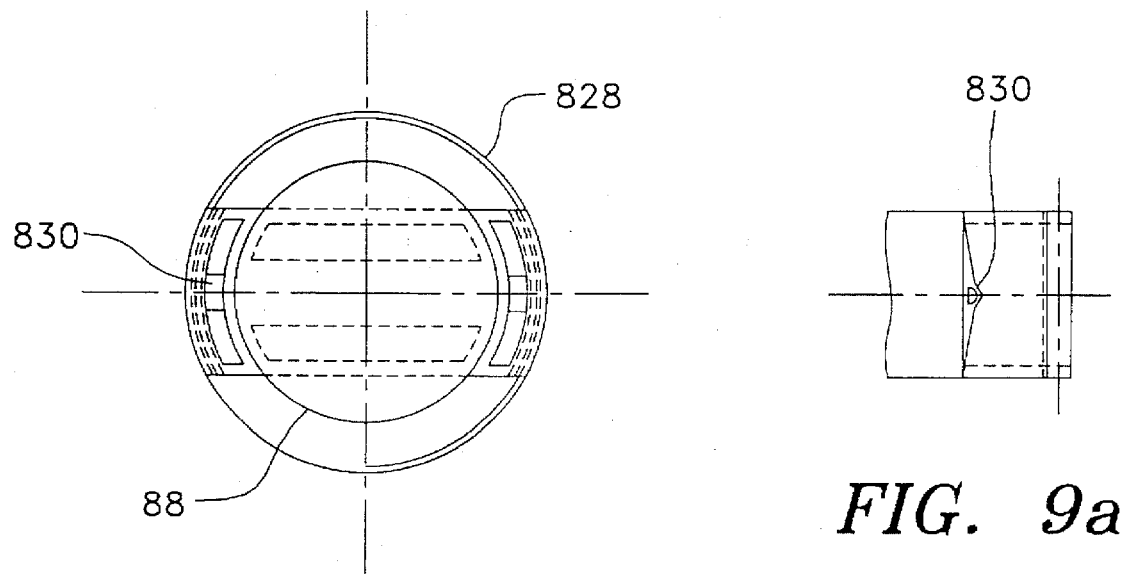
FIG. 9
FIG. 9a

DEVICE FOR THE INTENTIONAL AND CONTROLLABLE DISTRIBUTION OF A LIQUID OR VISCOUS MATERIAL

BACKGROUND OF THE INVENTION

1. Field of the Invention

The present invention relates to a device for controlling the distribution of a liquid or viscous material, and more specifically, to the feeding of small quantities of relatively valuable liquid or viscous substances according to a preassigned, precisely maintained time schedule. Automatic, autonomous control of the course of the program proceeds essentially without external intervention.

The invention further relates to refinements, improvements and an expansion of the field of application of conveyor mechanisms powered by gas evolution cells as the primary energy carrier for fluid to viscous media and similar materials to be conveyed.

In the narrower sense, the invention relates to an apparatus for selective controllable release of a liquid or a viscous mass or a suspension of solid particles in a liquid. The apparatus comprises a cylindrical container, a container seal with a screw or plug connection, a cylindrical piston fitting in the container with a sliding fit, dividing the latter into a compressed gas chamber and a mass chamber, with a ring-shaped seal around the circumference, and a component containing the electrical elements such as the electrochemical gas evolution cells, the adjustment mechanism, and the load resistors and contacts.

2. Description of the Prior Art

Devices for conveying liquid or semiliquid, viscous, greasy or doughy masses which make use of a compressed gas supplied by an electrochemical gas evolution cell as the force-exercising medium, are already known. Also known is the gas evolution cell itself, whose principle is based on electrochemical reactions in a primary element. In this cell, a gas, usually hydrogen, is released from the electrolyte. Since the gas evolution in electrochemical cells of this type depends only on the internal current, provided the other operating parameters are held constant, a proportional quantity of gas per unit time is delivered. Since the current depends on the total resistance of the closed circuit, it can be adjusted or controlled and regulated by external resistors. This results in an adjustability or controllability of gas production per unit time.

Of the numerous types of gas evolution cells available, only those which have a compact construction with a gas diffusion electrode are of interest. The cell is generally set in operation by closing the external circuit.

Devices which make use of a membrane or piston for conveying greasy materials are already known. In these devices, the membrane or piston acts as a pressure-transmitting structural component for expelling the lubricant as a function of time. Various other designs have been proposed in which, for instance, the gas generated expands an expandable body which in turn acts on a membrane or piston, or in which a cell is installed directly in the container lid or in the piston on the pressurized gas side of the device. In other cases, the lubricant is introduced into an initially closed pouch in the cylinder of the device and the pouch as a whole is exposed to the pressure of a piston. In all of the known piston arrangements, for operationally reliable separation of the compressed gas chamber from the mass chamber, special, usually ring-shaped sealing elements are used. This type of sealing is already known from piston machine construction in general. The container seal is usually provided with a screwed-on or fitted-on seal for the purpose of refilling with lubricant.

Other devices, including infusion devices which are used to convey solutions of pharmaceutical or medical agents to patients, are known. With these devices, it is common that the cylindrical vessels of ampules or infusion syringes are used as containers in which a piston driven by gas pressure moves. On the open end side of the container is an insert containing the gas generating and electrical control elements, for gastight sealing of the container. At the exit from the container, there is a push-on injection needle, a catheter or a throttling device.

The known devices for conveying masses by gas evolution cells as the primary energy carrier leave much to be desired in both their design and operational aspects. This is especially true of the details and the number of constituent components, maintenance, service life, refillability, reusability, especially of the valuable parts, robustness and operational reliability. The known designs are often too complicated in structure, too clumsy and subject too strongly to wear.

Therefore, a great need exists for a further development, improvement, refinement and simplification of such devices, in general, as well as in particular (lubricators, infusion devices, etc.).

The following documents are cited as state of the art:
DE-C-35 32 335
EP-B-0 278 954
DE-A-37 18 341
W0-88/09187
PCT/CH-89/00044

Summary of the Invention

One object of the present invention includes devising an apparatus for the selective and controllable release of a liquid, a viscous mass or a suspension of solid particles in a liquid, using the pressure exerted by a gas coming from an electrochemical gas evolution cell. The device should have a long service life, low wear and simple economical maintenance, with the most far-reaching possibilities of application and universality possible, be as simple as possible in structural design and be comprised of a minimum number of individual components. The replacement of elements subjected to consumption or wear and the refilling of the mass to be conveyed should be possible without fouling, and without corrosion or impairment of the electrical contacts. Special, separate sealing elements should be avoided wherever possible, if this offers advantages. Visual and acoustic indicators and warning devices should be of a simple and operationally reliable type. Finally, the device should be as economically produced as possible and suitable for economical mass production.

This problem is solved by the device of the present invention, which makes use of a tablet-shaped gas evolution cell. The cell is enclosed in a metal housing which receives a gas diffusion electrode, a counter electrode, and an aqueous electrolyte, and is activated through the operation of an external circuit. These electrical elements can either be housed within the bottom of the container, forming a monolithic structure, or connected to the container by a detachable screw or plug connection which is held by a clamping device to the bottom of the container. The container is further provided with a funnel-shaped seal at the opposite end of the container, which forms the mass chamber.

The invention is described with reference to the detailed description which is provided below, taken in conjunction with the following illustrations.

BRIEF DESCRIPTION OF THE DRAWINGS

FIG. 1 is an exploded sectional view of one embodiment of the present invention.

FIG. 1a is a side view of the plug connector of FIG. 1.

FIG. 4 is an exploded sectional view of an alternative embodiment of the present invention.

FIG. 4a is a side view of the plug connector of FIG. 4.

FIG. 4b is a partially sectioned, side view of a refilling device for the embodiment of FIG. 4.

FIG. 8 is a partially sectioned, side view of an alternative embodiment plug-shaped component of the present invention.

FIG. 9 is a partially sectioned, top view of the device of FIG. 8.

FIG. 9a is a partial sectional view of the contact of FIG. 9.

DETAILED DESCRIPTION OF THE INVENTION

Figure 2:
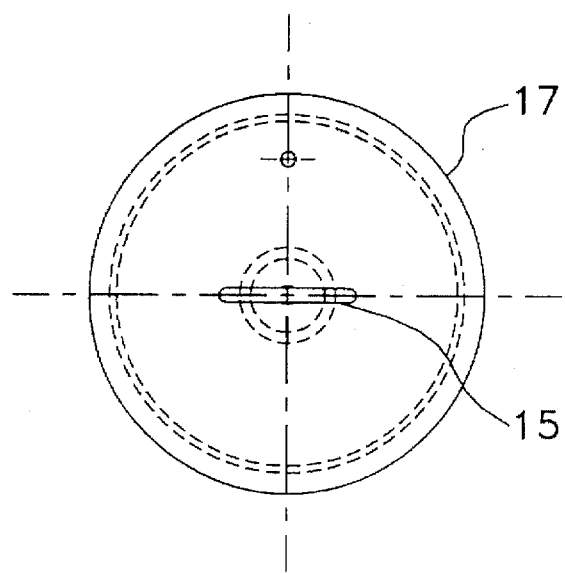
FIG. 2 is a top view of the external plug-shaped component of FIG. 1.

FIG. 1 is a schematic representation and longitudinal section (outline) of the basic structure of the device of the present invention, simultaneously showing a version of a lubricator. Component 1 is an essentially smooth cylindrical container of a shape-stable plastic which has a container bottom 11 with several offsets. The container bottom, as in the present case, is firmly connected to the container 1, either monolithically or separate from it, and is also designed with multiple divisions (for the latter compare FIG. 4). In the present case the container bottom 11 carries the clamping device 12 for the electrical elements (cell, resistor, contacts), which is monolithically connected to it and which extends into the interior of the container 1, and which includes two pairs of elastically springing tongues, provided with bulges, which stand orthogonally to one another. At the end of the container 1 there is a container seal 2 connected to the container by a tight connection with, in the present case, a screw connection 3 (for a plug connection, see FIG. 10). The piston 6 includes, in the present case, two parts of elastic plastic which can be tightly plugged into one another, together with the piston sliding surface, to form a chamber 74 for a radially protruding annular seal (which forms a film of grease) in the form of a lip and a pot-shaped recess/depression 13. The piston 6 divides the contents of the container into a compressed gas chamber 4 and a mass chamber 5. The recess/depression 13 is of great importance for keeping the compressed gas chamber 4 small in the interest of the shortest possible start-up time for the piston 6.

The electrical elements used in the clamping device 12 are the gas evolution cell 8 (in the present case a double cell), the adjustment and load resistor 9 (here a potentiometer) and the contact 10, as depicted in FIG. 1a. In the container bottom 11 is an external (pluggable) plug-shaped component 17 provided on its flange with a scale 80 and on its pipe-like neck 21 with an inwardly extending profiled pivot/peg 15, in the form of a rotatable disk for adjusting the resistor 9. In this case the pivot/peg 15 (in the present case displaying a cross-shaped cross section) engages a corresponding opening of the rotating resistor 9. Component 16 is an O-ring for sealing between the components 11 and 17. For clarity, the individual parts of the device are shown in an exploded view. This view also illustrates the sequence of assembly steps.

FIG. 2 shows the basic outline of the outer plug-shaped component for adjusting the load resistor of a lubricator. The component 17 on the bottom side of its flange has a stop cam which engages a circular groove of the container bottom 11, which does not encompass a full circle but rather ends in the corresponding stops. With this the end positions of the adjustment of the resistor are defined. Component 15 is the cross-shaped pivot/peg in profile. On the top side of its flange the component 17 has a radial activation slot.

Figure 3:
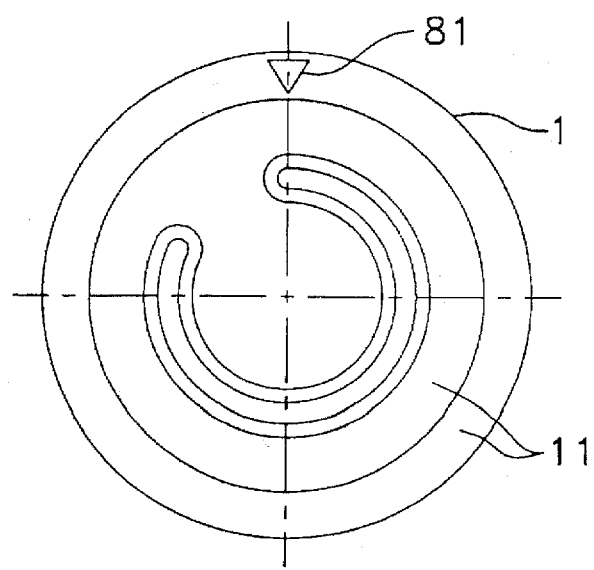
FIG. 3 is a top view of the container of FIG. 1.

In FIG. 3 the basic outline of the container (container bottom side) of a lubricator is shown. Component 1 is the container, and component 11 is the container bottom, which has a groove for engaging stops in the stop cam of component 17. Component 81 is the marking arrow for the scale 80 (cf. FIG. 1).

FIGS. 4, 4a and 4b show a longitudinal section (outline) of one version of a lubricator with replaceable electrical elements. The reference numbers 1, 2, 3, 4, 5, 6, 7, 8, 9, 10, 12, 13 and 74 correspond in form and function exactly to those of FIG. 1. The container bottom 411 is divided and consists of the actual offset container bottom 411, with a threaded central opening and the outer pluggable and inner screwable plug-shaped components 417 and 418. The container bottom 411 is provided with an annular groove 477 and a scale 480. Structure 417 is a rotatable component while structure 418 is screwed fast to the container bottom, by threading. Component 419 is a disk-shaped flange carrying a marking arrow 481 for the scale 480, of the outer component 417, while 421 represents its pipe-like neck and 415 the profiled pivot/peg. The inner component 418 has a disk-like flange 420 and a pipe-like neck 422 as well as the clamping device 12 for electrical elements. The flange 420 on its inner side carries the peripheral cam 476 for fixation of the end position. Also on the end face of flange 420, an outer annular groove 423 and inner annular groove 424 are provided in which to engage the outer cam 425 or the inner cam 426 of the outer component 417. Structure 427 is the O-ring between the container bottom 411 and the inner component 418. Structure 416 is the O-ring between the container bottom and the outer component 417. As an accessory a refilling device 479, as shown in FIG. 4b, is provided in the form of a cartridge equipped with folding bellows and an internal threaded adapter nipple. For clarity the individual parts are shown in an exploded view.

Figure 5:
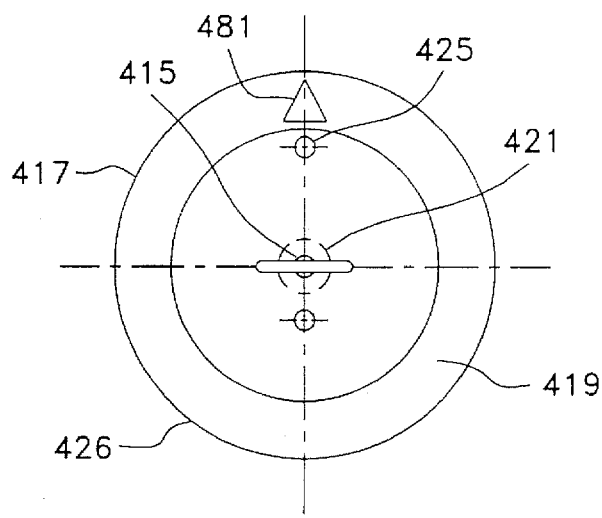
FIG. 5 is a top view of the external plug-shaped component of FIG. 4.

FIG. 5 shows the basic outline of the outer plug-shaped component of a lubricator with replaceable electrical elements, such as are shown in FIG. 4. Structure 417 is the outer plug-shaped rotatable component whose disk-like flange 419 carries on its outer side a triangular marking arrow 418 for the scale. The flange 419 is also provided with a central radial activation slot. On the inner side of structure 419 are the cams 425 and 426 (shown as broken lines). The profiled pivot/peg 415 and the pipe-shaped neck 421 are also indicated (broken lines).

Figure 6:
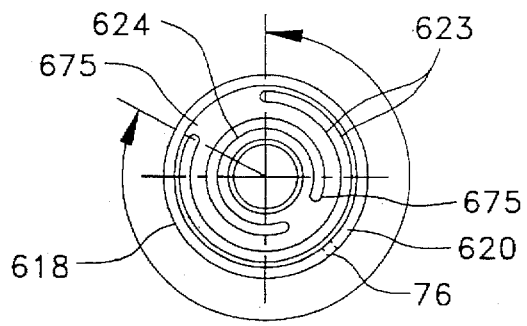
FIG. 6 is a top view of the internal plug-shaped component of FIG. 4.

FIG. 6 shows the outline of an internal plug-shaped component of a lubricator with replaceable electrical elements. Structure 618 represents the internal plug-shaped component with its disk-shaped flange 620, into whose outer side the outer annular groove 623 and the inner annular groove 624 are received. Grooves 623 and 624 in each case do not cover an entire circle but rather end in the corresponding semicircular stops 675 to limit the movement of the rotatable outer component 617. The maximum achievable angle of rotation is indicated by a circle with arrow points.

Figure 7:
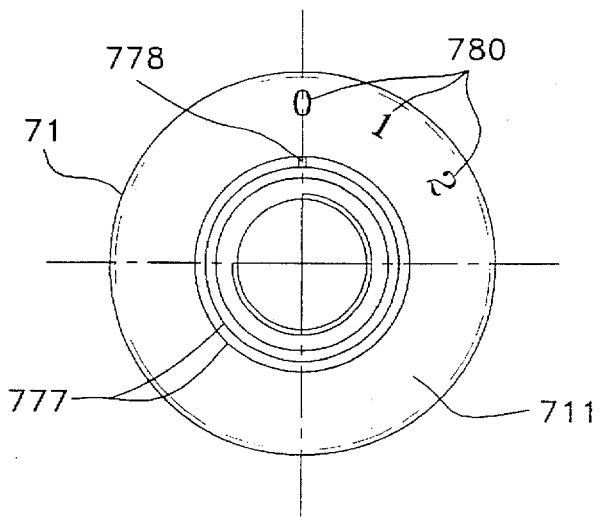
FIG. 7 is a top view of the container of FIG. 4.

FIG. 7 shows the outline of the container of a lubricator with replaceable electrical elements. Structure 71 is the container, and structure 711 is the actual container bottom with the annular grooves 777, with stops 778 and a central threaded opening for receiving the inner screwable plug-shaped component 718. The container bottom 711 has a scale 780 for indicating the relative position of the flange 719 of the outer plug-shaped rotatable component 717.

FIG. 8 is a schematic longitudinal section of one version of the device for small dimensions (cartridges). The container and piston are omitted in this figure for simplicity. The hollow-cylindrical container does not have an actual container bottom but ends in the form of an open pipe segment. The place and the function of the container bottom are assumed by the outer pot-shaped component 828 and the inner pot-shaped component 831, designed as the turning knob. The outer component 828 (displaying a scale 880 on its end side) is connected by a plug or screw connection to the hollow cylindrical end of the container (not shown). Component 828 is connected by a notch to a radially positioned, elastic spring leaf retainer 829 containing a snap-in bulge 889. The spring leaf retainer 829 serves to hold the gas evolution cell 88. The axially arranged contact 830 (sliding contact) is integrated into the spring leaf retainer 829. The inner pot-shaped component 831 on its inner end face carries the annular adjusting resistor 89 (potentiometer) and the central contact 866 firmly connected to it, which completes the current circuit to the cell 88. Component 831 is provided on its end side with a marking arrow 881 for the scale. Between the container and the outer pot-shaped component 828, and between the container and the inner pot-shaped component 831, there is in each case an O-ring 864, 865 as a sealing element.

FIG. 9 is a schematic cross section of one version of the inner part of the device for small dimensions (cartridges). Structure 828 is the outline of the offset part of the outer pot-shaped component. Component 830, as shown in FIG. 9a, represents the axially arranged contact with a radial contact tongue (sliding contact). This contact 830 is shown once more in FIG. 9a. Structure 88 is the cylindrical, tablet-shaped, single gas evolution cell.

Figure 10A:
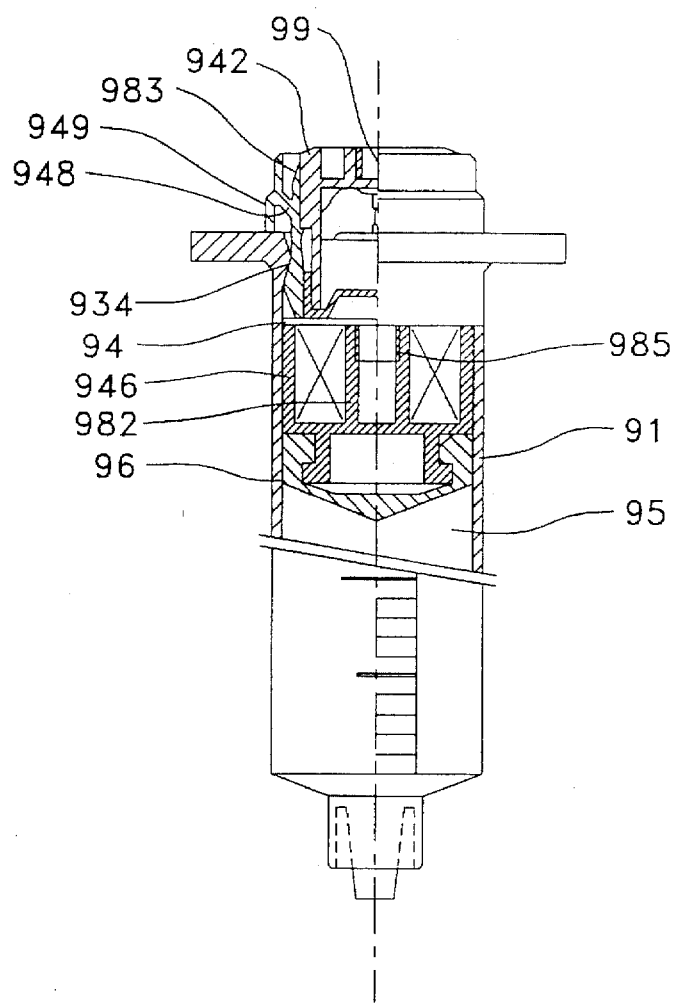
FIG. 10a is a partially sectioned, side view of an infusion syringe in accordance with the present invention, depicting a normal arrangement of the components.
Figure 10B:
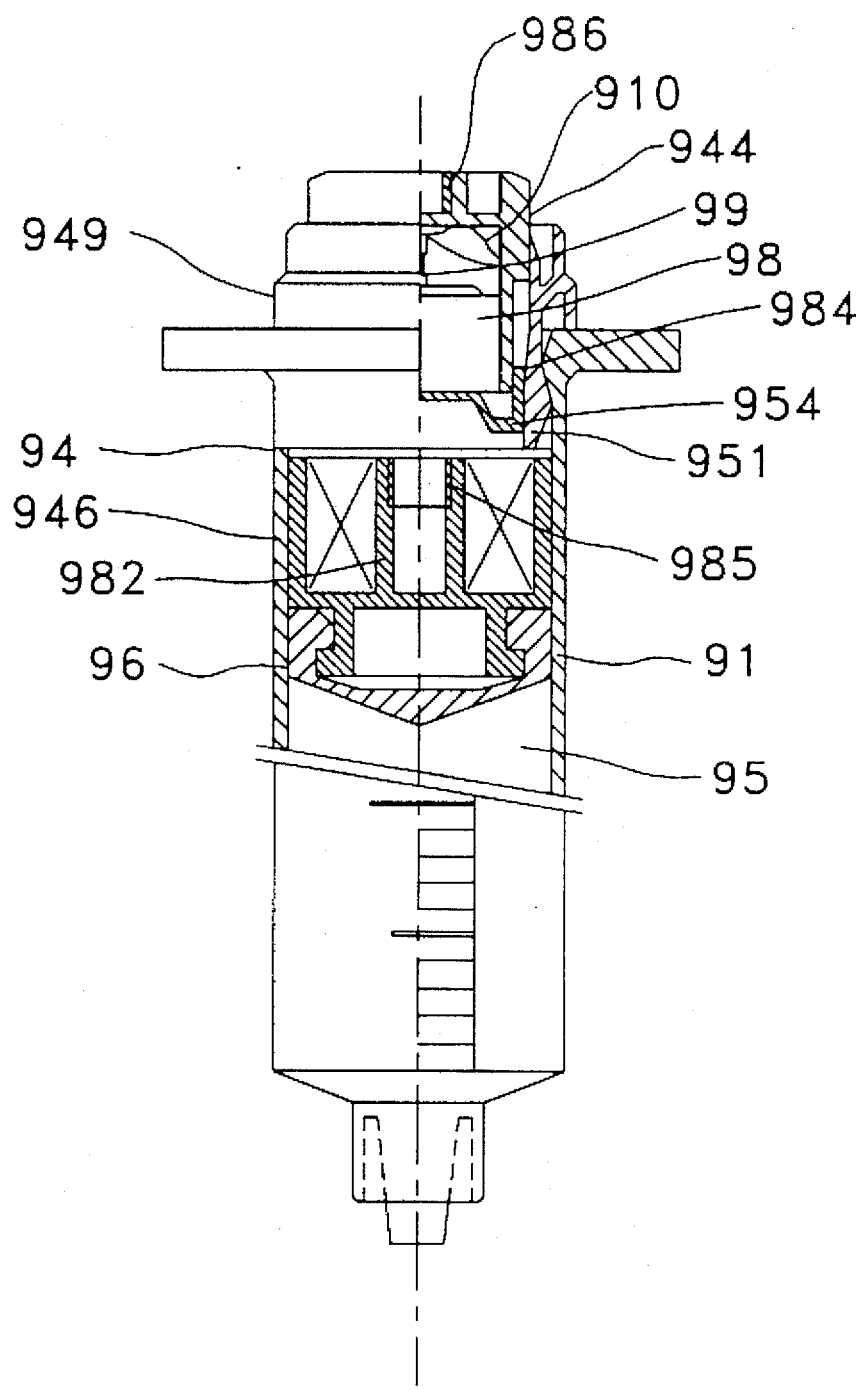
FIG. 10b is a partially sectioned, side view of the infusion syringe of FIG. 10a, depicting an arrangement of components responsive to increased pressure in the gas chamber.

FIGS. 10a and 10b show partial, longitudinal sections of a first embodiment of an infusion syringe. FIG. 10a depicts a normal arrangement of the components, and FIG. 10b depicts an arrangement of the components with an impermissible amount of pressure in the gas chamber. The shape and dimensions of the container 91 correspond to those of a standard conventional graduated infusion syringe with a conical plug connection (to receive an injection needle or a catheter). The container 91 on its flange-side end displays an inwardly projecting bulge 934. Structure 94 is the pressurized gas chamber, structure 95 is the mass chamber for receiving the in-flowing liquid, and structure 96 is a multipartite piston, with an inner piston core 982 and a threading 985 for receiving an activation rod (to pull the medium up). The piston also has a vane-shaped guide rib 946. Component 948 is an external, radial-elastic sleeve whose stop ring 949 lies on the flange of the container 91. The outer sleeve 948 has a radially inwardly resilient sealing lip 983 and several internal conical offsets 951, as well as an inwardly protruding stop bulge 984. An internal, hollow pressing/sealing plug 942 extends into the sleeve 948, which on its outer jacket surface contains at least one axially running air evacuation opening 944 in the form of a narrow slot and which on its outer end includes a threading 986 for an activation rod (for disassembly). Between sleeve 948 and plug 942 is an axially/radially elastic locking/snap ring 954 which simultaneously serves to hold the gas evolution cell 98 and the frictional fixation of the fixed rod-shaped resistor 99 and the U-shaped resilient contact 910. The normal operating position is shown in FIG. 10a. The initial position before start-up is shown in FIG. 10b.

Figure 11:
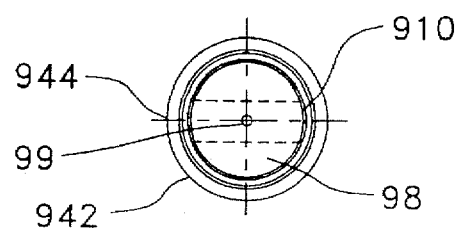
FIG. 11 is a partially sectioned, top view of the infusion syringe of FIGS. 10a and 10b.

FIG. 11 shows a cross section of one version of an infusion syringe. The inwardly lying, hollow pressing/sealing plug 942 on its outer circumference running along the jacket line displays axially running air evacuation openings 944 mutually offset by 90° (in the form of slight notches). Structure 98 is the gas evolution cell 99, with the rod-shaped resistor shown in broken lines (viewed from the profile), and structure 910 is the U-shaped resilient contact, which fits closely with its legs on the inner contour of the cylindrical hollow space of the plug 942.

Figure 12A:
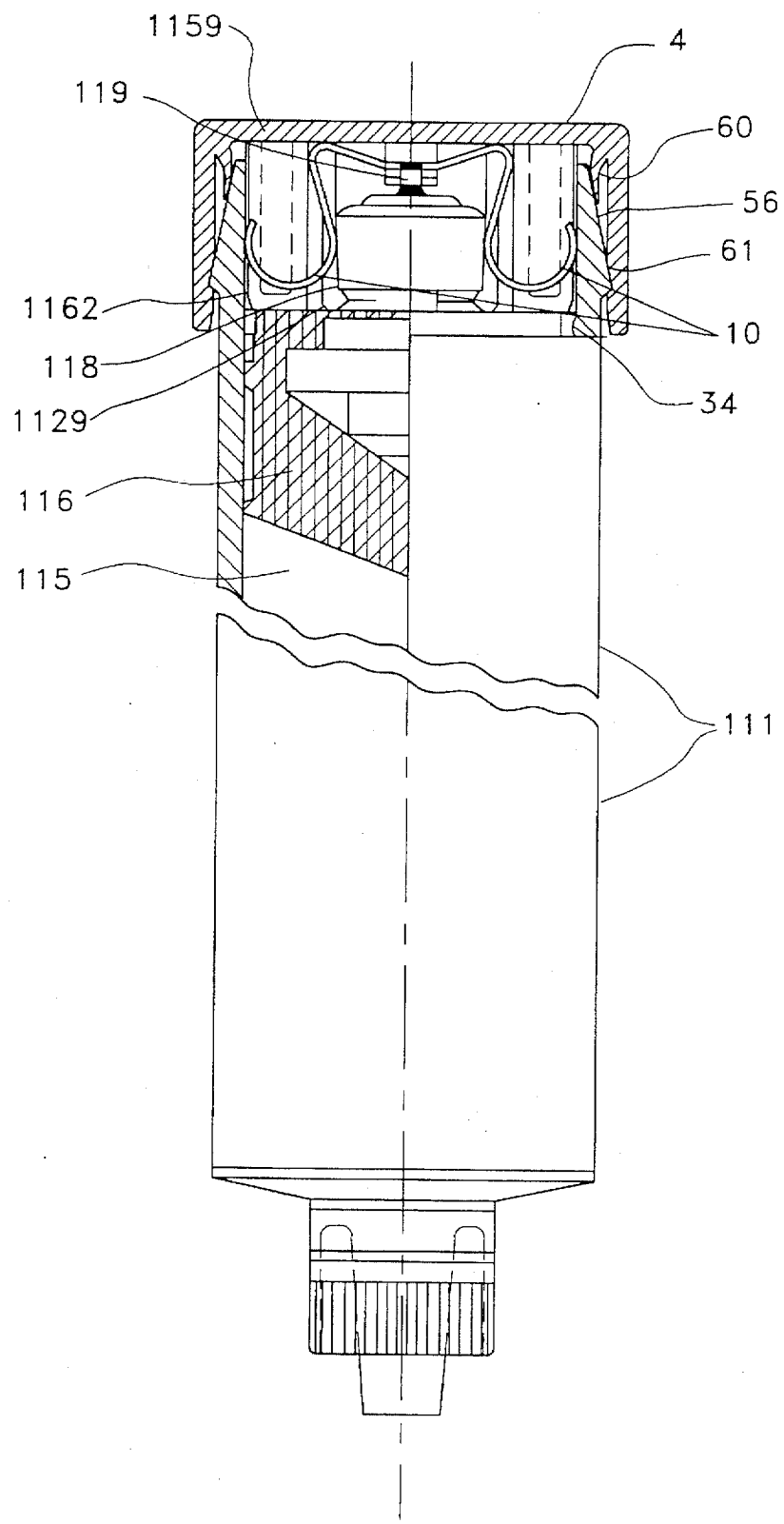
FIG. 12a is a partially sectioned, side view of an alternative embodiment of an infusion syringe, depicting the piston of the syringe.
Figure 12B:
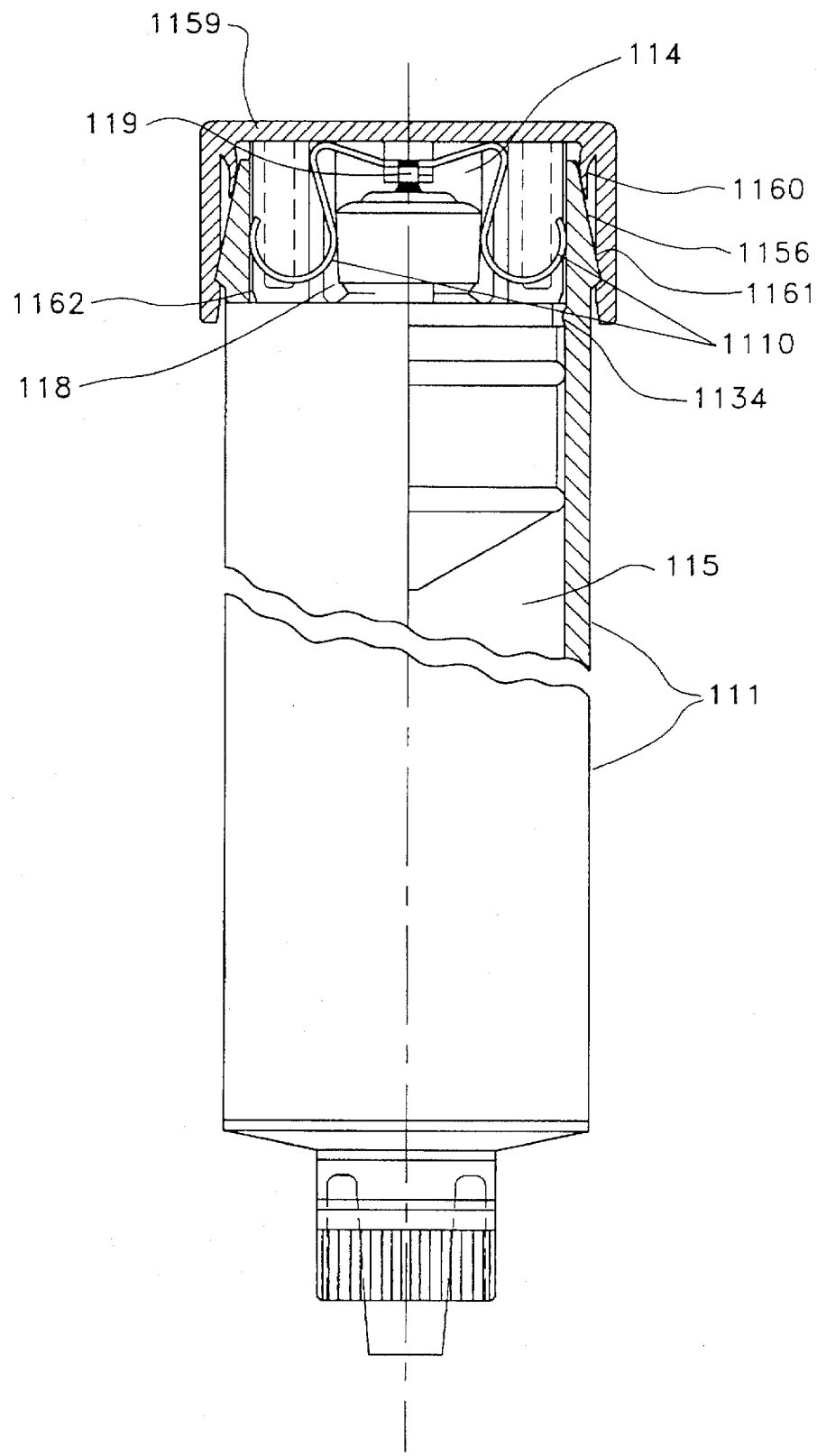
FIG. 12b is a partially sectioned, side view of the infusion syringe of FIG. 12a, depicting the compressed gas chamber and the mass chamber.

FIGS. 12a and 12b show partial, longitudinal sections of an alternative embodiment infusion syringe. FIG. 12a depicts the multipartite piston of the syringe, and FIG. 12b depicts the compressed gas chamber and the mass chamber. Structure 111 is the container of a conventional commercial graduated infusion syringe with a conical plug connection. Component 114 represents the compressed gas chamber and component 115 is the mass chamber. Component 116 is a usually multipartite piston. The container 111 at its open end has an inwardly protruding bulge 1134 as a safety stop for the piston 116 and an outwardly lying conical shoulder 1156. The function of the container bottom is assumed by a radially elastic cap 1159 serving as a closing lid which displays at its inner corner a radially inwardly acting resilient sealing lip 1160 and an inwardly lying conical recess 1161. The edge of the conical shoulder 1156 of the container 111 engages the recess. The elastic cap 1159 is additionally equipped in its central part with radially positioned, radially inwardly and axially outwardly acting hook-shaped spring leaf retainers 1129 to hold the gas evolution cell 118, and in its part lying farther to the outside, with axial guide ribs 1162 to hold the double S-shaped contacts 1110. Component 119 is the fixed load resistor.

Figure 13:
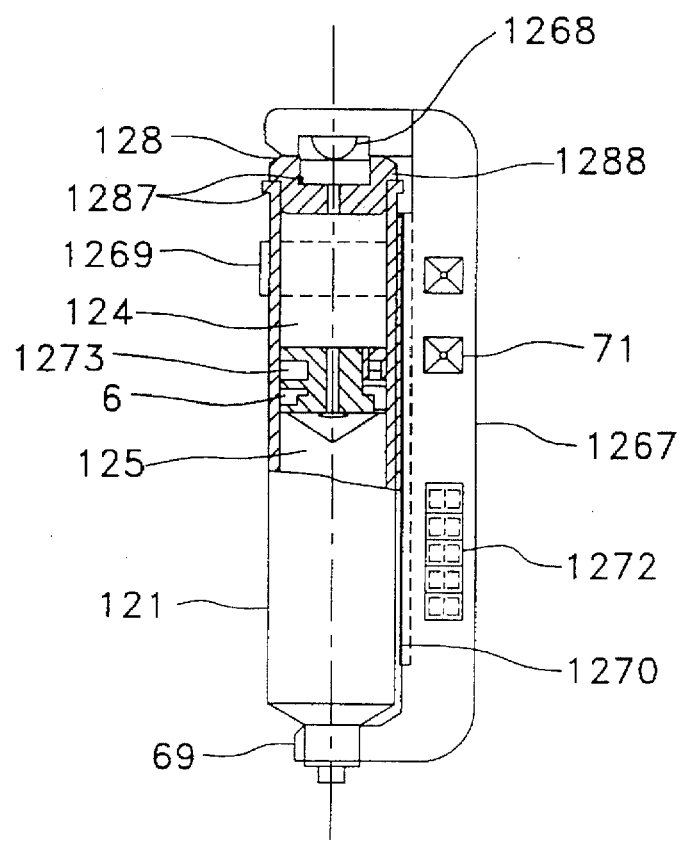
FIG. 13 is a partially sectioned, side view of a path measuring device for an infusion syringe.

FIG. 13 is a longitudinal section (outline) of a path-measuring device for an infusion syringe. Structure 121 is the container, with the compressed gas chamber 124 and the mass chamber 125. Structure 1267 is a U-shaped housing which has on one of its end sides an axial stop contact 1268, and in the other part, several clamp jaws 1269 to hold the infusion syringe, as well as a linear coil 1270, push buttons 127, and an indicator 1272. A radial contact 1288 is additionally arranged between the tablet-shaped gas evolution cell 128 and the housing 1267. Otherwise the usual seals 1287 for closing the gas chamber 124 are provided. The piston is equipped with a permanent magnet 1273 which controls the position of the piston, and with it the mechanism of movement of the piston, by its electromagnetic coupling with the linear coil.

Figure 14:
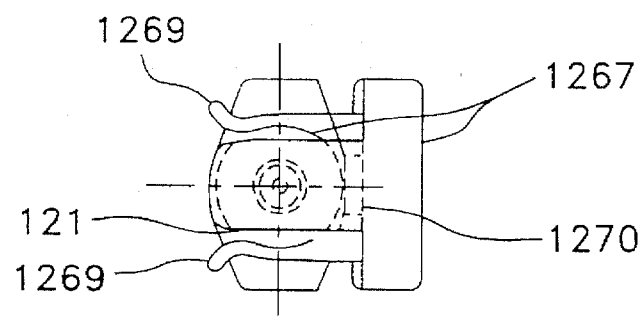
FIG. 14 is a top view of the path measuring device of FIG. 13.

FIG. 14 shows an outline of the path-measuring device for an infusion syringe. The reference numbers 121, 1267, 1269 and 1270 correspond exactly to those in FIG. 13 and require no further explanation. Note the space-saving design of this apparatus.

EXAMPLE 1

See FIGS. 4, 4a, 4b, 5, 6 and 7

The device is designed as an automatic lubricator with exchangeability of the electrical elements (as well as the possibility of refilling with lubricant) that is maintenance free in operation. The lubricator generally includes a hollow cylindrical container 1 of transparent shape-stable plastic, the container seal 2 with a screw or plug connection 3, the piston 6, the outer plug-shaped component 417, the inner plug-shaped component 418 and the electrical elements 8, 9 and 10. In the present case the container seal 2 is made of elastic plastic with a corrugated funnel for the purpose of flexibility under impact and vibrational stress. The piston 6 is made up of two parts and at the pressure-chamber end has an elastic sealing lip 7 which is prestressed in diameter and which in operation fits closely on the inner wall of the container 1. The sealing lip 7 together with the cylindrical sliding face of smaller diameter defines the space 74 for the grease film, thus creating ideal sealing and lubricating relationships for the piston 6. The piston has a pot-shaped recess/depression 13 for minimizing the dead volume in the compressed gas chamber 4 and in order to achieve the shortest possible start-up time of the piston after it is put into operation. The container bottom 411 carries the scale 480 and is provided with a groove 477 with stop 478. The inner component 418 includes a shape-stable solid plastic on its pipe-shaped neck 422, and in the present case, has a threading with which it is screwed into a corresponding inner threading in the opening of the container bottom 411. The clamping device 12 serves to hold the electrical elements, gas evolution cell 8, rotating resistor (potentiometer) 9 and contacts 10, and includes two pairs of resilient tongue-like grippers which essentially hold the double cell 8 firmly in all directions. The electrical elements 8, 9, 10 in the present case are firmly welded together to form a compact unit. This has the advantage that upon disassembly, or replacement, no contact and fouling problems arise. The elements 8, 9, 10 may, however, be installed in a common cassette as a variant. The outer plug-shaped component 417 is designed to be plugged in and engages (with its elastic pipe-like neck 421) a correspondingly offset boring in the inner component 418. The profiled pivot/peg 415 for transmitting the rotary motion to the potentiometer 9 in the present case has a cross-shaped cross section (12 corners). The cams 425 and 426 of the outer component 417 engage corresponding annular grooves 623 and 624 of the inner component 618, with their stops 675 thus limiting the rotary movements (see figure description). The peripheral cam 76 of the inner component 618 moves in the grooves 777 in the container bottom (fixation of the end position). The running time is set by adjusting the outer component 417 provided with the marking arrow 481 relative to the scale 480 on the container bottom 411. The refilling device 479 is designed as a folding bellows, and may for this purpose be screwed on to the threading of the screw connection 3.

EXAMPLE 2

See FIGS. 8, 9 and 9a

This is a version of the apparatus for relatively small dimension, so-called cartridges. The outer pot-like component 828 carrying the circular-ring scale 880 is of a shape-stable plastic. It is sealed against the container by the O-ring 864 and against the rotating (turning knob) inner pot-like component 831 (also of plastic) by the O-ring 865 in a gastight manner. The outer component 828 on its neck-like offset inner end has two notches into which the leaf spring retainers 829 are snapped in a radially resilient manner by means of the snap-in bulge 889, for assembly and disassembly. The leaf spring retainer 829 is designed in the region of contact with the outer component 828 in the form of segments, and the segments are admitted into the latter. Preferably the leaf spring retainer 829 includes corrosion-resistant, highly resilient metal material. The bottom of 829 serves as an axial spring for retaining the gas evolution cell 88, and curves inward. To change and replace the gas evolution cell 88 the leaf spring retainer 829 is pulled manually axially away from the outer pot-like component 828, the spent cell 88 is removed, and a new one is inserted. The entire assembly in then replaced axially on the component 828. The desired quantity of gas per unit time is set by turning the inner pot-shaped component 831, the relative position between the marking arrow 881 and the scale 880 on the inside of the outer pot-like component 828 being a measure of gas production. Operation at different temperatures is allowed for by the fact that the scale 880 is designed with different graduations.

EXAMPLE 3

See FIGS. 10a, 10b and 11

In the present case the device represents an automatically operating infusion instrument which generally releases a constant quantity per unit time of a certain infusion solution to the patient. As a rule and for this purpose, the container 91 of the vessel used is made of a conventional standard hollow cylindrical infusion syringe. Into the threading 985 of the piston core 982 a metal or plastic activation rod (piston rod) is screwed, and with its aid the medium to be administered is pulled by the motion of the piston up to the inwardly protruding bulge 934 on the container 91, serving as a stop. The outer lying radially elastic sleeve 948 (of a flexible plastic) is forced axially into the container 91, together with the interior-positioned hollow pressing/sealing plug 942 including the electrical elements 98, 99, 910, and is manufactured of shape-stable plastic. This occurs until the stop ring 949 comes to lie on the flange of the container 91. By means of the locking/snap-in ring 954 which engages the inwardly lying conical shoulder 951 of the radial elastic sleeve 948, the latter is pressed radially outward and clamped in and sealed gastight behind the inwardly projecting bulge 934 of the container 91 (FIG. 10a). Upon insertion of the plug 942 the gas evolution cell 98 is switched on via resistor 99, while simultaneously a precompression of the gas (air) is achieved in the compressed gas chamber 94 so that the start-up time of the piston 96 is shortened. The gas evolution cell 98 is held in part by friction and in part by spring tension over contact 910. For disassembly and replacement of the gas evolution cell 98 the above mentioned activation rod is screwed into the threading 986 of the pressing/sealing plug 942 and the latter is pulled out axially until the electrical elements 98, 99 910 are accessible and the old gas evolution cell can be removed and replaced by a new one. In the case of an impermissible overpressure in the compressed gas chamber 94 the inwardly lying pressing/ sealing plug 942 is forced axially outward by overcoming its friction in normal operation until its axial air evacuation openings 944 come to stand above the height of the sealing lip 983 of the outward lying radial elastic sleeve 948. At this time the locking snap-in ring 954 remains in its position and serves as an axial guide for the inwardly lying hollow pressing/sealing plug 942. The gas evolution cell 98 at this time, due to its radial adhesive friction with the contact 910, is pushed outward together with the plug 942 without interrupting its gas evolution. In this way the path for pressure relief is opened via the air release openings 944. In the case of external mechanical blocking of the plug 942 the overpressure can be released via the radially prestressed sealing lips 983, by their expansion in a safe manner (double safety). After the pressure is released the normal operating position can be restored by pressing the pressing/sealing plug 942 axially in, by hand, thus restoring the operational conveying of the medium.

The invention is not limited to the examples.

The device for selective controllable release of a liquid or a viscous mass or a suspension of solid particles in a liquid, with reference to FIG. 1 (and the like numerals of FIG. 4), includes a cylindrical container 1 and a container seal 2 with a screw or plug connection 3, a cylindrical piston 6 fitting in the container 1 with a sliding fit, separating the latter into a compressed gas chamber 4 and a mass chamber 5, an annular seal 7 on the circumference and a component containing the electrical elements such as the electrochemical gas evolution cells 8, adjusting and loading resistors 9 and contacts 10. The gas evolution cell 8 displays a tablet-shaped construction of metal closed on all sides, a gas diffusion electrode, an aqueous electrolyte and a counterelectrode, and can be activated by closing an outer current circuit. The component containing the electrical elements (8, 9, 10) of the container bottom 11 forms a monolithic structure with a container 1 or is connected to the container via a detachable screw or plug connection. The electrical elements (8, 9, 10) are held in place by a clamping device 12 and are provided on the mass chamber side end of the container 1 with a funnel-shaped container seal 2. The piston 8 on the compressed gas chamber side is advantageously provided with a protruding annular sealing lip 7, creating a chamber 74 for a grease film, and in the central part with a pot-like recess/depression 13 reducing the compressed gas chamber 4 to a minimum. The container seal 2 is designed in the form of a funnel-shaped elastic corrugated closing lid with a threaded nipple, where the electrical elements 8, 9, 10 (designed in compact form as a double cell with electrical resistor) are held via a clamping device 12 directly in the container bottom 11. The container bottom 11 is provided with a marking arrow 81 for the scale. Also provided in the container bottom 11 is a rotating plug-shaped component 17 (having a scale 80 and O-ring 16) having a pipe-like neck 21 for adjustable electrical resistor 9 (designed as a rotary potentiometer), which has a profiled pivot/peg 15 which engages a corresponding opening in the rotary potentiometer with a sliding fit.

The electrical elements (8, 9, 10) are designed in compact form as a double cell with an electrical resistor and are preferably held indirectly via a clamping device 12 in the container bottom 11, provided with the scale 80, the latter being divided several times for the purpose of exchangeability and replaceability of the electrical elements (8, 9 10) and refillability of the medium being conveyed. The container bottom contains in the central part at least two rotationally symmetrical components (17, 18) which can be plugged into one another coaxially, each displaying a disk-like flange (19, 20) and a neck (21, 22), and which are disassemblable. Such structure is provided with a groove (23, 24), limited by the stop 75 and cams (25, 26), with snapping and gripping mechanisms for mutual fixation and for holding the gas evolution cells 8 and the resistors 9 (designed as rotary potentiometers). To this end, such structure is equipped with at least one pluggable component 17, with a profile pivot/peg 15 which engages a corresponding opening of the rotary potentiometer with a sliding fit. Preferably a first internal rotationally symmetrical plug-shaped component 18 is present, and is provided with a clamping device 12 with inwardly directed resilient tongues for holding the cylindrical knob-shaped gas evolution cells 8 and the rotary adjustable resistor 9. To this end, a disk-like flange 20 with a peripheral cam 76 is provided for engaging a groove 77 (with stop 78) of the container bottom 11, and has a pipe-like neck 22 with outer threading, which can be screwed into a corresponding internal threading in a central opening of the offset container bottom 11. In addition, a second external (also plug-shaped) component 17 is present, provided with a marking arrow 81 for the scale 80, which is designed to be pluggable into the first component by means of a pipe-like radially flexible snapping closure (in this case, both between the container bottom 11 via a circular depression and the first component 18 and also between the container bottom via a depression and the second component 17, with one O-ring 426, 427 for each connection, as shown in FIG. 4). Such structure is arranged as a seal and, in addition, a refilling device 79 is provided in the form of a folding bellows-like cartridge with an internally threaded attachment.

In a preferred version the container bottom 11 containing the electrical elements (8, 9, 10) is divided. An outer pot-like component 28 is sealed against the neighboring structural elements by O-rings (864,865, as shown in FIG. 8) and is capable of being screwed to the cylindrical container end. A scale 80 is provided with a radially inwardly and axially outwardly acting, centrally-symmetrically arranged spring leaf retainer 29, clamped on via a snap-in bulge 89, in order to hold the individual cell 8 as well as an axially arranged contact 30 with a radial contact tongue. An internal rotationally symmetrically component 31 capable of being pressed into the outer component 28 and displaying a marking arrow 81 for the scale carries a circular ring-shaped adjusting resistor 9 and a central contact 66 firmly connected to it.

In one variant of the device, as shown in FIGS. 10a, 10b and 11, the cylindrical container 91 corresponds to the graduated vessel of a standardized infusion syringe. At the bottom side the device has an inwardly projecting bulge 934, with a piston 96 having several parts including a piston core 982 and a threading 985 for activation rods, to pull up the medium. The device is further provided with radially positioned vane-shaped guide ribs 946. The component forming the container bottom 911 (containing the electrical elements 98, 99, 910) includes an outwardly lying, rotationally symmetrical, radially elastic sleeve 948 provided with a stop ring 949, an end side sealing lip 983, an inwardly projecting stop bulge 984 and several inwardly lying conical shoulders 951. An inwardly lying, rotationally symmetrical, hollow pressing/sealing plug 942 is equipped at its open end with a radially/axially resilient inner locking/snap-in ring 954 and air evacuation openings 944 for pressure relief, which carries in its outer end face an internal threading 986 for activation rods (for disassembly). Finally, the electrical elements (98, 99, 910) include a single, axially mounted cylindrical cell 98, a short axially positioned solid electrical rod resistor 99 and resilient contacts 910 formed as U-/S-shaped curved bands.

In another variant corresponding to an infusion syringe, as shown in FIGS. 12a and 12b, the cylindrical container 111 on the bottom-side end has an outwardly protruding conical shoulder 1156 and an inwardly projecting bead or bulge 1134, where a piston 116 is provided. The component forming the container bottom 11 contains the electrical elements (118, 119, 1110) and includes a single rotationally symmetrical, essentially radially elastic cap 1159. The elastic cap 1159 serves as a closing lid. Such structure includes an inwardly lying resilient sealing lip 1160 and an inwardly lying conical indentation 1161 which engages the conical shoulder 1156 of the container 111 and a radially inward and axially outward-acting, centrally symmetrically arranged leaf spring retainers 1129 for holding the single cell 118. Axially positioned guide ribs 1162 are provided for the strap-shaped contacts 1110. Finally, the electrical elements (118, 119, 1110) include an axially mounted cylindrical single cell 118, a short axially positioned fixed electrical rod resistor 119 and resilient contacts 1110 formed from double S-shaped curved strips or bands.

In a special version, as shown in FIGS. 13 and 14, the cylindrical container 121 sealed by the seal 1287 is connected mechanically to a path-measuring device including a U-shaped housing 1267, an axial stop contact 1268, a radial contact 1288 between the gas evolution cell 128 and the housing 1267, clamp jaws 1269, a linear coil 1270, push buttons 1271 and an indicator 1272 (via the clamp jaw 1269 and the stop contact 1268, and electrically, via the contacts 1268, 1288). The piston 6 is equipped in its interior with a permanent magnet 1273 acting on the coil 1270.

The path-measuring device serves for controllable gas production and for the limitation of gas production (in the limiting case, to zero).

ADVANTAGES OF THE INVENTION

General and Lubricators

Hygienic, simple and practical refilling of the mass to be conveyed without disassembly of the container seal is possible.

Combination of electrical elements to form a compact unit; no contact, corrosion and fouling problems.

Flawless piston sealing forming a monolithic unit with the piston without special sealing elements such as piston rings, etc.; self-sealing, self-lubricating, without disadvantageous stripping off of grease.

Low piston friction; therefore small path hysteresis and low start-up force required. Container closure fully elastic, insensitive to vibration and shock.

Infusion Device

Applicability of standard infusion syringes makes special manufacture of containers unnecessary.

Visual overpressure indicator.

Simple hygienic and environmentally friendly exchangeability of the gas evolution cell.

Double safety against impermissibly high overpressure.

Simple construction of multifunctional structural elements; omission of special sealing and fixing elements.

Path-Measurinq Instrument

Simple separation of tasks between mechanical disposable part and electrical device (microprocessor).

Continuously variable program control not limited by any factors or limitations.

Acoustic and visual warning in the case of deviations from nominal operation.

I claim:

1. A device for selective, controllable release of a fluid, a viscous mass or a suspension of solid particles in a fluid, comprising:

a cylindrical container;

a top enclosing a first end of the container, in combination with a funnel-shaped container seal;

a bottom enclosing a second end of the container opposite to the first end, wherein the bottom includes a clamping device for receiving electrical components, the electrical components including an electrochemical gas evolution cell, an adjustable load resistor and electrical contacts which combine to develop an external current circuit, wherein the gas evolution cell has a tablet-shaped construction including a metal enclosure receiving a gas diffusion electrode, a counter electrode and an aqueous electrolyte, and wherein the external current circuit is connected with the gas evolution cell to activate the gas evolution cell; and a cylindrical piston slidingly received within the container and dividing the container into a pressurized gas chamber and a mass chamber, wherein the funnel-shaped container seal faces the mass chamber of the container, and wherein the piston includes a circumference provided with an annular seal and a coupled pair of coaxial plugs for causing telescoping movement of the piston 2. The device of claim 1 wherein the top further includes a screw connector.

3. The device of claim 1 wherein the top further includes a plug connector.

4. The device of claim 1 wherein the bottom and the container form a monolithic structure.

5. The device of claim 1 wherein the bottom and the container are joined by a screw connector.

6. The device of claim 1 wherein the bottom and the container are joined by a plug connector.

7. The device of claim 1 wherein portions of the piston facing the pressurized gas chamber are provided with a protruding ring-shaped sealing lip, defining a space for receiving a grease film, and wherein central portions of the piston include a pot-like recess for reducing the pressurized gas chamber to a minimum size.

8. The device of claim 7 wherein the container seal is formed as a funnel-shaped, elastic, corrugated sealing cover having a threaded nipple.

9. The device of claim 8 wherein the external current circuit includes two gas evolution cells which, together with the resistor, are held by the clamping device directly to the bottom of the container.

10. The device of claim 9 wherein the bottom of the container further includes a marking arrow, forming an adjusting scale.

11. The device of claim 10 which further includes a rotating, plug-shaped component having a pipe-like neck with a profiled peg for slidingly engaging an opening in a rotary potentiometer.

12. The device of claim 11 which further includes an O-ring for sealing the plug-shaped component to the bottom of the container.

13. The device of claim 11 wherein the bottom of the container further includes an adjusting scale.

14. The device of claim 1 wherein portions of the piston facing the pressurized gas chamber are provided with a chamber for receiving a protruding annular sealing lip for developing a film of grease, and wherein central portions of the piston include a pot-like recess for reducing the pressurized gas chamber to a minimum size.

15. The device of claim 14 wherein the container seal is formed as a funnel-shaped, elastic, corrugated sealing cover having a threaded nipple.

16. The device of claim 15 wherein the external current circuit includes two gas evolution cells which, together with the resistor, are held by the clamping device directly to the bottom of the container.

17. The device of claim 16 wherein the bottom of the container further includes a marking arrow, forming an adjusting scale.

18. The device of claim 17 wherein the bottom of the container includes a plurality of chambers exchangeably and replaceably receiving the electrical components of the clamping device.

19. The device of claim 18 wherein central portions of the bottom of the container include two rotationally symmetrical, coaxially connected components, each having a disk-shaped flange with a neck, a groove which is limited by a stop and cams, and snap-fit gripping means for mutually fixing and holding the gas evolution cells.

20. The device of claim 19 which further includes a rotary potentiometer, and wherein at least one of the rotationally symmetrical components includes a profiled peg for slidingly engaging an opening in the rotary potentiometer.

21. The device of claim 20 wherein one of the rotationally symmetrical components is an inner plug-shaped component provided with a clamping device having inwardly directed resilient tongues for holding gas evolution cells and the rotary potentiometer, and wherein the plug-shaped component further includes a disk-like flange with a peripheral cam for engaging a groove with a stop associated with the bottom of the container, and a threaded pipe-like neck for engaging a correspondingly threaded central opening in the bottom of the container.

22. The device of claim 21 wherein another of the rotationally symmetrical components is an outer plug-shaped component having a marking arrow forming an adjusting scale, and a pipe-like, radially flexible, snap-fit closure for engaging the inner plug-shaped component.

23. The device of claim 22 which further includes a sealing O-ring positioned between the bottom of the container, through a circular depression, and the inner plug-shaped component, and between the bottom of the container, through a depression, and the outer plug-shaped component.

24. The device of claim 23 which further includes a refilling device formed as a folding bellows-like cartridge with internal threads for attachment to the device.

25. The device of claim 1 wherein the bottom of the container is divided, and receives an outer pot-like component including a scale and having threads for engaging the second end of the container, and wherein O-rings seal the outer pot-like component against the container.

26. The device of claim 25 which further includes radially inwardly and axially outwardly acting, centrally-symmetrically arranged leaf spring retainers having snap-in bulges for clamping a single gas evolution cell to an axially arranged contact with a radial contact tongue, and an inner rotationally symmetrical component pressed into an outer component and including a marking arrow forming a scale, wherein the rotationally symmetrical component includes a circular, ring-shaped adjusting resistor connected with a central contact.

27. The device of claim 1 wherein the container is a graduated vessel of an infusion syringe, and wherein one of the plugs of the piston is threaded to receive an activation rod for infusing a medium.

28. The device of claim 27 wherein the plugs are separated by an internally locking snap-in ring.

29. The device of claim 28 wherein the plugs include an outwardly-lying, rotationally symmetrical sleeve and an inwardly-lying, rotationally symmetrical, hollow-pressed sealing plug.

30. The device of claim 29 wherein the container includes a stop bulge formed on inner portions of the container, for limiting withdrawal of the sleeve from the container.

31. The device of claim 30 wherein the sleeve includes a stop ring for engaging a flange formed on the container, for limiting movement of the sleeve into the container.

32. The device of claim 31 wherein the sealing plug includes an air evacuation opening for releasing an overpressure from the pressurized gas chamber responsive to telescoping of the sealing plug relative to the sleeve.

33. The device of claim 27 which includes a single gas evolution cell, an axially positioned, fixed electrical rod resistor, and spring contacts formed of curved bands.

34. The device of claim 1 wherein the container is a graduated vessel of an infusion syringe, wherein the bottom of the container has an outwardly projecting conical shoulder and an inwardly projecting bulge, and wherein the bottom of the container includes a single, rotationally symmetrical elastic cap forming a closure lid with an inner, resilient sealing lip.

35. The device of claim 34 which further includes an inner, conical recess which engages the conical shoulder of the container, radially inwardly and axially outwardly acting, centrally symmetrical leaf spring retainers for holding the single gas evolution cell, and axially positioned guide ribs forming strap-shaped contacts.

36. The device of claim 35 which includes a single, axially mounted gas evolution cell, an axially positioned, fixed electrical rod resistor, and resilient contacts formed as curved bands with a double S-shape.

37. The device of claim 1 wherein the container is enclosed by a seal and is firmly mechanically connected with a path-measuring device including a U-shaped housing, an axial stop contact, a radial contact between the gas evolution cell and the housing, clamp jaws, a linear coil, push buttons and an indicator, which are mechanically connected by the clamp jaws and the stop contact, and which are electrically connected by the electrical contacts, and wherein the interior of the piston includes a permanent magnet for acting on the coil.

* * * * *